United States Patent [19]

Collins

[11] Patent Number: 5,042,878

[45] Date of Patent: Aug. 27, 1991

[54] INVALID CHAIR RESTRAINT

[76] Inventor: Elsie O. Collins, 1617 Luck Ave., Knoxville, Tenn. 37917

[21] Appl. No.: 495,645

[22] Filed: Mar. 19, 1990

Related U.S. Application Data

[63] Continuation of Ser. No. 387,009, Jul. 31, 1989, abandoned.

[51] Int. Cl.$^5$ ............................................. A47C 31/00
[52] U.S. Cl. ..................................... 297/467; 297/465
[58] Field of Search ............... 292/467, 468, 465, 219; 297/464

[56] References Cited

U.S. PATENT DOCUMENTS

| | | | |
|---|---|---|---|
| 3,713,692 | 1/1973 | McCracken et al. | 297/467 |
| 4,037,764 | 7/1977 | Almosnino et al. | 297/467 X |
| 4,050,737 | 9/1977 | Jordan | 297/465 |
| 4,139,131 | 2/1979 | Hathaway | 297/467 X |
| 4,232,898 | 11/1980 | Bodrero | 297/219 |
| 4,235,474 | 11/1980 | Rosenberg | 297/465 |
| 4,428,514 | 1/1984 | Elf | 297/467 X |
| 4,702,323 | 10/1987 | Schradel et al. | 297/467 X |
| 4,834,460 | 5/1989 | Herwig | 297/467 X |
| 4,871,210 | 10/1989 | Alexander et al. | 297/467 X |

FOREIGN PATENT DOCUMENTS 0649206 5/1985 Switzerland ........................ 297/467

1590172 5/1981 United Kingdom ............... 297/467

Primary Examiner—José V. Chen
Attorney, Agent, or Firm—Pitts and Brittian

[57] ABSTRACT

An invalid chair restraint for securing a patient in a chair (or wheelchair) in a substantially upright and seated position. The restraint includes a back portion which is releasably secured to the back of the chair with a securing strap that extends from opposite edges of the back portion. This back portion is integrally formed with a seat portion which is dimensioned for receiving the lower to mid torso of the patient. In this connection, the seat portion includes a section upon which the patient is seated, and a crotch strap that extends between the legs of the patient. A body securing element is releasably joined to the distal end of the crotch strap, with this body securing element embracing the patient for holding the torso of the patient in a desired and substantially upright posture. In the preferred embodiment, this body securing element is a pair of straps that pass over the shoulders of the patient and releasably engage the securing strap that embraces the back of the chair. Further, in this preferred embodiment, the body securing element is joined to the crotch strap with fasteners that permit the effective length of the body securing element to be adjusted.

4 Claims, 3 Drawing Sheets

INVALID CHAIR RESTRAINT

This is a Continuation-in-Part application based upon a parent application of the applicant, namely Ser. No. 387,009 filed July 31, 1989, now abandoned.

DESCRIPTION

1. Field of Invention

The present invention concerns an invalid chair restraint, and more particularly a restraint designed for securing an invalid to a chair, wheel chair or the like such that the invalid is prevented from slipping out of the chair and is further maintained in a position of proper posture.

2. Background Art

Invalids such as elderly or physically disabled persons are often confined to chairs, wheelchairs or like devices. It is important that such persons be secured to prevent them from sliding out of the chair or bending to a position of poor posture. Known prior art devices directed towards the problem of securing or harnessing individuals in chairs are disclosed in the following U.S. Pat. Nos.: 3,940,166; 3,954,280; 4,235,474; 4,632,425; 4,715,618; and 4,728,119.

While various of the prior art patents are directed to devices designed for securing or restraining individuals in a seated position, the present invention has as an object to provide a device to restrain an invalid person in a chair or wheelchair at a position approximating appropriate posture.

It is another object of the present invention to provide an invalid chair restraint which prevents the invalid from sliding forward in the chair.

It is a further object of the present invention to provide a restraint that can be readily installed on a conventional chair having an upright back or on a wheelchair having handles which protrude upwardly and outwardly from the upper portion of the back, these handles facilitating the pushing the patient over a supporting surface.

An additional object is to provide a restraint designed such that it can be inexpensively manufactured and is readily washable when fabricated from cloth or cloth-like materials which are readily washable.

DISCLOSURE OF THE INVENTION

Other objects and advantages of the present invention will be accomplished by the present invention which provides an invalid chair restraint for holding elderly and/or invalid patients in a position approximating proper posture. The device of the present invention includes a back portion which is releasably secured to the chair. In the preferred embodiment, the back portion can be readily mounted on a wheelchair having handles which extend upwardly and outwardly from the upward back portion thereof. A seat portion serves to releasably secure the lower to mid torso of the patient. In this regard, the seat portion includes a crotch strap which extends from a section of the seat portion upon which the patient sits, between the legs of the patient, to a location proximate the lower or mid torso. This crotch strap is releasably secured to the patient, in the preferred embodiment, via straps that pass over the shoulders of the patient such that the patient is held in a position to prevent sliding forward and/or bending at the waist in order to maintain the patient in a normally upright position.

BEST MODE FOR CARRYING OUT THE INVENTION

Figure 1:
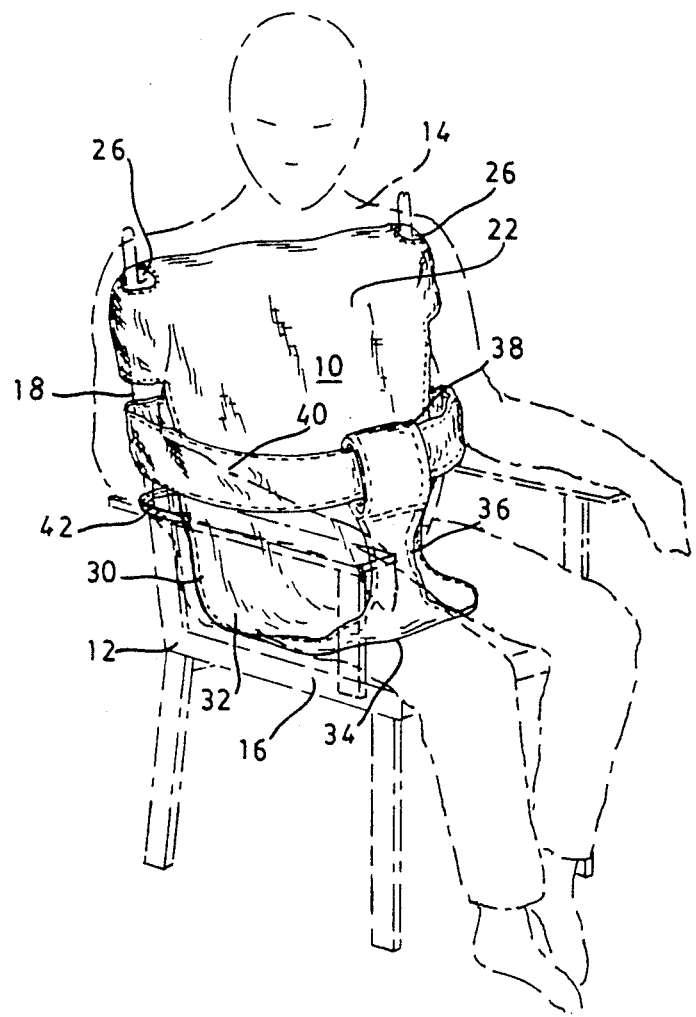
FIG. 1 illustrates an invalid chair restraint constructed in accordance with various features of the present invention which is releasably secured to a chair and which defines a seat portion for receiving the lower to mid torso portion of the patient.
Figure 2:
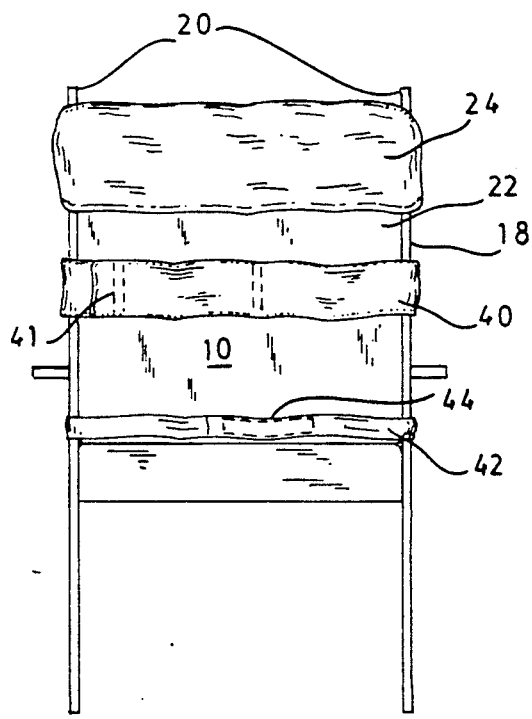
FIG. 2 illustrates the chair restraint as shown in FIG. 1 as seen from the rearward portion of the chair.
Figure 3:
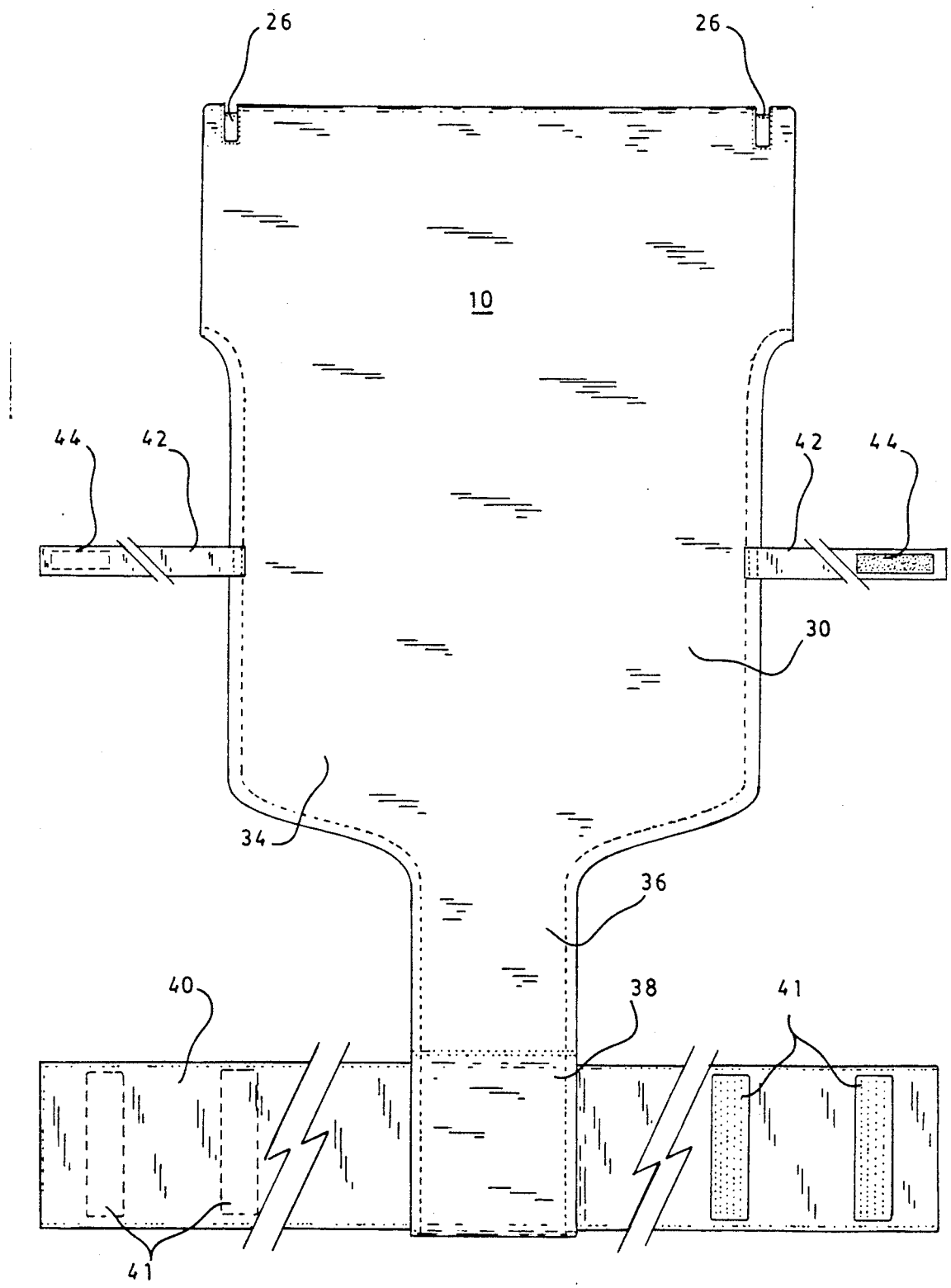
FIG. 3 illustrates a plan view of the invalid chair restraint shown in FIGS. 1 and 2.

An invalid chair restraint constructed in accordance with various features of the present invention is illustrated generally at 10 in FIGS. 1-3. This chair restraint is designed for releasably securing an invalid, such as a disabled or elderly person, in a chair and for maintaining that person in a position approximating proper posture. Moreover, the chair restraint serves to prevent the patient from sliding forward in the seat of a chair.

As will be seen in FIG. 1, the invalid chair restraint 10 is designed for being used in connection with a suitable and conventional chair 12 for restraining a patient 14 in a position such that this patient does not slide forward in the seat 16 of the chair. The chair 12 illustrated has a back 18 which terminates at its upper portion in the upright members 20.

The chair restraint 10 includes a back portion 22 that is releasably secured to the back 18 of the chair. In the embodiment illustrated, the back portion 22 is joined with the upper portion of the chair back 18 by top securing means 24. The top securing means 24 in this embodiment defines a cavity which receives the upper portion of the chair back 18 therein, thus preventing the chair restraint from being pulled either downwardly or away from the back by forces normally exerted on the restraint by an invalid. This back portion 22 proximate the top securing means 24 includes a pair of openings 26 shown in FIGS. 1 and 3. These openings 26 serve to receive the upright members 20 of the chair or handles of a wheelchair therethrough with the receipt of the upright members or wheelchair handles through the openings 26 serving to further secure the position of the back portion 22 on the back 18 of the chair. Thus, the restraint 10 can be readily used in connection with either a regular chair or with a wheelchair.

The back portion 22 of the restraint 10 is integrally formed in this embodiment with a seat portion generally indicated at 30. This seat portion 30 serves to receive the lower to mid torso of the invalid. In this regard, the seat portion 30 includes a seat section generally indicated at 32. This section 32 terminates proximate its forward portion 34 in a crotch strap 36 that extends from the seat section 32 between the legs of the patient and to a location proximate the forward torso as shown in FIG. 1. The crotch strap 36 in this embodiment terminates in an eyelet 38 that is designed for receiving a torso strap 40. This torso strap, when threaded through the eyelet 38 of the crotch strap 36, is wrapped about the patient and the chair and joined at its opposite ends by suitable hook and loop type fasteners 41 illustrated in FIG. 2. Thus, the torso strap 40 serves as securing means for releasably securing the patient in the seat portion 30 supported on the chair seat 16.

In order to maintain the back portion 22 of the restraint 10 against the back 18 of the chair, a securing strap 42 extends from opposite sides of the back portion 22 of the restraint 10 and is dimensioned for being wrapped about the back portion 18 of the chair 12 to hold the restraint in proper orientation on the chair. This strap 42 is also provided, in the preferred embodiment, with suitable hook and loop type fasteners 44 (see FIG. 2) at its opposite ends for releasably securing the strap 42 to the chair.

While hook and loop type fasteners have been described and illustrated in connection with the torso strap 40 and the securing strap 42, which serves to hold the back portion 22 of the restraint 10 on the chair, it will be recognized by those skilled in the art that buckles or other suitable fastening means such as snaps could be used. However, the hook and loop type fasteners do provide adjustability and perform well.

Figure 4:
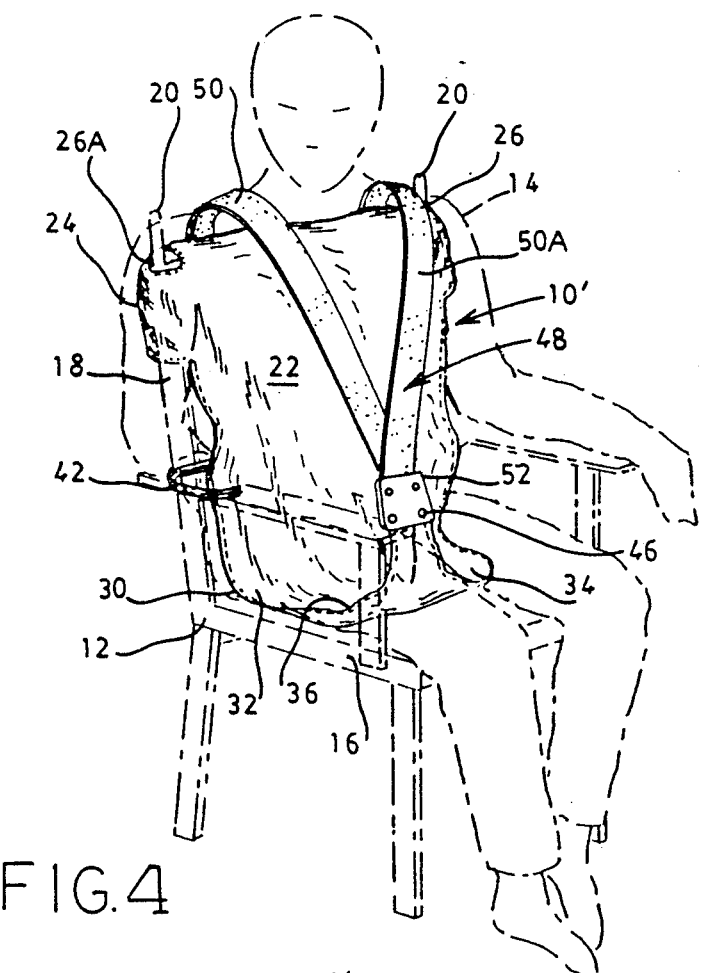
FIG. 4 illustrates another embodiment of an invalid chair restraint useful for maintaining a patient in a chair or wheelchair in a normally upright position.

Another, and preferred, embodiment of the present invention is illustrated at 10' in FIG. 4. All components that are the same as those of the embodiment of FIGS. 1-3 carry the same identification numerals. Where the components are similar, but slightly modified, they carry the same identification numeral although primed. In this FIG. 4, portions of the chair 12 and patient 14 (both in phantom lines) have been deleted to better show the chair restraint 10'. This embodiment of the chair restraint 10' also has a back portion 22 which is joined to the upper portion of the chair back 18 by a top securing means 24. This top securing means, in this preferred embodiment, also defines a cavity with receives the upper portion of the chair back 18 therein, thus preventing the chair restraint from being pulled either downwardly or away from the back by forces normally exerted on the restraint by an invalid. This back portion 22, proximate the top securing means 24, includes a pair of openings 26, 26A. These openings 26, 26A serve to receive any upright projections 20 of the chair back, or to receive handles of a wheelchair therethrough. Thus, this restraint 10' can be used with either ordinary chairs or wheel chairs.

The back portion 22 of the restraint 10' is integrally formed in the preferred embodiment with a seat portion generally indicated at 30. This seat portion 30 serves to receive the lower to mid torso of the invalid. In this regard, the seat portion includes a section generally indicated at 32 which terminates proximate its forward portion 34 in a crotch strap 36' that extends from the seat section 32 between the legs of the patient and to a location proximate the forward torso as shown. The outer end of the crotch strap 36' is releasably attached, as with snaps 46, to a body support means 48 having a pair of straps 50, 50A adapted to individually pass over the shoulders of the patient 14, as shown. The juncture at 52, between the crotch strap 36' and the body support means 48, which juncture utilizes the snaps 46, also provides for adjusting the relative total length from the seat portion 30 to the extreme ends of the straps 50, 50A. This is accomplished by having a plurality of the snaps 46 at different positions on the respective pieces being joined thereby.

As in the earlier described embodiment of FIGS. 1-3, this embodiment of the restraint 10' is provided with a securing strap 42 that extends from opposite sides of the back portion 22. This securing strap is designed to encircle the back of the chair so as to secure the back portion of the restraint to the chair at all times. This strap 42 is provided in the preferred embodiment with suitable hook and loop types fasteners at its opposite ends as indicated at 44 (see FIG. 6).

Figure 5:
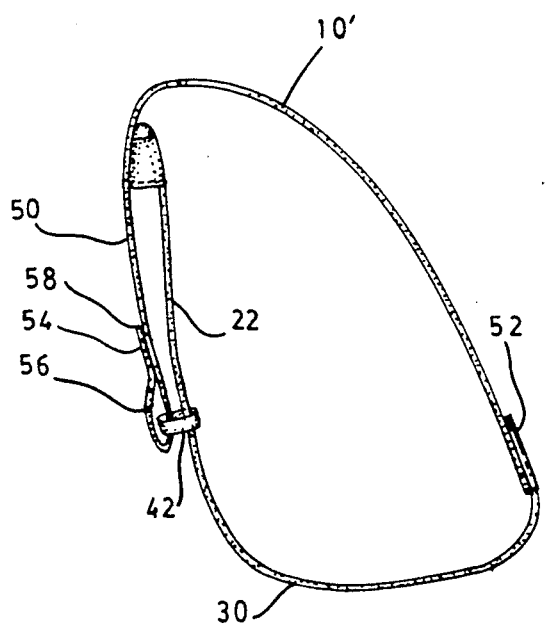
FIG. 5 is a side elevational view of the embodiment of the restraint illustrated in FIG. 4 without the phantom insert of a patient.
Figure 6:
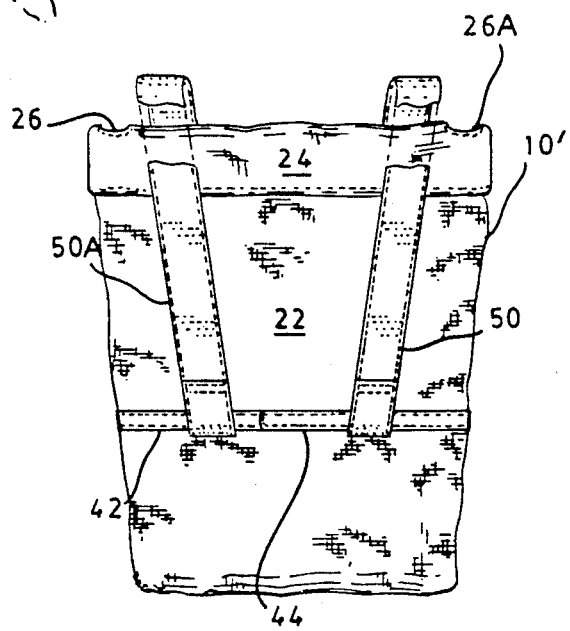
FIG. 6 is a rear elevational view, partially cut away, of the embodiment of the restraint illustrated in FIG. 5.

A side elevation of the embodiment of FIG. 4, without the chair or patient illustrated, is shown in FIG. 5. It can be seen that the terminal ends 54 of the straps 50 are formed into an eyelet 56. This eyelet 56 can be permanently formed, or preferably the terminal ends can be provided with hook and loop type fasteners (or any other form of fasteners) as at 58. By providing fasteners of this type at several locations, further adjustment of the effective length of the straps 50 can be effected. The aforementioned securing strap 42 passes through the eyelet 56 thus formed in both shoulder straps 50 so as to secure the ends of the straps 50 at the rear of the chair. This construction is also illustrated in FIG. 6. Thus these straps 50, by passing over the shoulders of the patient and engaging with the securing strap 42, maintain the patient in an upright position when the restraint 10' is in use.

From the foregoing detailed description, it will be recognized that an invalid chair restraint has been described and illustrated which is suitable for releasably securing an invalid in a chair or wheelchair. The restraint serves to prevent the invalid from sliding forward out of the seat of the chair, and further assists in maintaining the invalid in a substantially upright portion approximating proper posture. The device is preferably fabricated from cloth or other washable material such that it can be readily cleansed after continuous use or soiling. The seat portion of the device which serves to receive the lower to mid torso of the patient and releasably secures the patient therein, can be dimensioned as by adjusting the length of the crotch strap 36 such that a selected portion of the lower to mid torso of the invalid is secured thereby. The torso strap 40 wraps about the patient and, in this embodiment, the back 18 of the chair as is seen in FIG. 2 for firmly but releasably securing the patient in the desired posture. With the torso strap 40 wrapped about the back of the chair, it is impossible for the patient to slide forward without first releasing the fasteners 41 of the torso strap 40. In the embodiment of FIG. 4, the shoulder straps provide for securing the patient in position.

While various embodiments of the invention have been described and illustrated, there are modifications and alternate embodiments that can be constructed without departing from the spirit and scope of the invention described in the attached claims and equivalents thereof.

I claim:

1. An invalid chair restraint for supporting an invalid in a chair in a substantially normal seated position, said chair defining a chair back, said chair restraint comprising:
    a back portion defining a top portion, a bottom portion and opposite edge portions, said top portion of said back portion defining a pocket to receive a top edge of said chair back;
    a securing strap attached to said opposite edge portions of said back portion for being received around said chair back to secure said back portion to said chair, said securing strap having two aligned portions each having a first end attached to said back portion and a distal end, said distal ends each provided with releasable fastening means for joining said distal ends together to secure said back portion against said chair back;

a seat portion joined to said back portion at said bottom portion thereof, said seat portion for receiving the lower to mid torso portion of said invalid, said seat portion terminating in a crotch strap for insertion between legs of said invalid, said crotch strap having a distal end; and a pair of shoulder embracing straps joined to said distal end of said crotch strap, said shoulder embracing straps for passing over the shoulders of said invalid and over said chair back to terminate and be fastened to said securing strap at a point rearward of said chair back to prevent said invalid from sliding out of said chair and to maintain said torso of said invalid in an upright position within said chair, each said shoulder embracing strap having a distal end portion defining an eyelet for receiving said securing strap whereby said shoulder embracing strap is secured to said securing strap.

2. The chair restraint of claim 1 wherein said distal end portion of each said shoulder embracing strap defines a terminal end portion, and is provided with a first fastening component disposed proximate said terminal end portion and is provided with at least one second fastening component displaced upon said shoulder embracing strap from said first fastening component for releasably engaging said first fastening component, whereby said eyelet of said shoulder embracing strap is releasably formed by securing said first fastening component to said second fastening component.

3. The chair restraint of claim 2 wherein said distal end portion of each said shoulder embracing strap is provided with a plurality of said second fastening components selectively spaced along said shoulder embracing strap, whereby the effective length of said shoulder embracing strap is adjusted by the selective engagement of said first fastening component with one of said second fastening components.

4. An invalid chair restraint for supporting an invalid in a chair in an approximately normal position, which comprises:

a back portion defining a top portion, a bottom portion and opposite edge portions, said top portion of said back portion defining a pocket to receive a top edge of said chair, said pocket having openings in a top edge to receive projections of said chair therethrough;

a securing strap attached to said opposite edge portions of said back portion, said securing strap having two aligned portions each having a first end attached to said back portion and a distal end, said distal ends each provided with releasable fastening means for joining said distal ends together to secure said back portion against a back of said chair;

a seat portion integrally joined to said back portion at said bottom portion thereof, said seat portion for receiving the lower to mid torso portion of said invalid, said seat portion terminating in a crotch strap for insertion between legs of said invalid, said crotch strap having a distal end; and a pair of shoulder embracing straps releasably joined to said distal end of said crotch strap, said shoulder embracing straps for passing over the shoulders of said invalid and over the back of said chair to terminate and for being fastened to said securing strap at a point rearward of said chair back to prevent said invalid from sliding out of said chair and to maintain said torso of said invalid in an upright position within said chair, each said shoulder embracing strap having a distal end portion defining and eyelet for receiving said securing strap whereby said shoulder embracing strap is secured to said securing strap, said distal end portion of each said shoulder embracing strap defining a terminal end portion and being provided with a first fastening component disposed proximate said terminal end portion and being provided with a plurality of selectively spaced second fastening component displaced upon said should embracing strap from said first fastening component for releasably engaging said first fastening component, whereby said eyelet of said shoulder embracing strap is releasably formed by securing said first fastening component to one of said second fastening components and whereby the effective length of said shoulder embracing strap is adjusted by the selective engagement of said first fastening component with one of said second fastening components.

* * * * *